US010589013B2

(12) United States Patent
Bourque

(10) Patent No.: US 10,589,013 B2
(45) Date of Patent: Mar. 17, 2020

(54) PROSTHETIC RIB WITH INTEGRATED PERCUTANEOUS CONNECTOR FOR VENTRICULAR ASSIST DEVICES

(71) Applicant: TC1 LLC, St. Paul, MN (US)

(72) Inventor: Kevin Bourque, Reading, MA (US)

(73) Assignee: TCI LLC, St. Paul, MN (US)

( * ) Notice: Subject to any disclaimer, the term of this patent is extended or adjusted under 35 U.S.C. 154(b) by 49 days.

(21) Appl. No.: 15/685,976

(22) Filed: Aug. 24, 2017

(65) Prior Publication Data

US 2018/0055983 A1   Mar. 1, 2018

Related U.S. Application Data

(60) Provisional application No. 62/380,081, filed on Aug. 26, 2016.

(51) Int. Cl.
| | |
|---|---|
| *A61M 1/10* | (2006.01) |
| *A61M 1/12* | (2006.01) |
| *A61F 2/30* | (2006.01) |
| *A61F 2/28* | (2006.01) |
| *A61F 2/48* | (2006.01) |

(52) U.S. Cl.
CPC ......... *A61M 1/127* (2013.01); *A61F 2/30744* (2013.01); *A61M 1/1008* (2014.02); *A61M 1/122* (2014.02); *A61F 2/28* (2013.01); *A61F 2002/3067* (2013.01); *A61F 2002/30224* (2013.01); *A61F 2002/30589* (2013.01); *A61F 2002/30604* (2013.01); *A61F 2002/482* (2013.01); *A61M 2205/04* (2013.01); *A61M 2205/8262* (2013.01)

(58) Field of Classification Search
CPC ....................................................... A61M 1/10
See application file for complete search history.

(56) References Cited

U.S. PATENT DOCUMENTS

| | | | |
|---|---|---|---|
| 4,925,443 | A | 5/1990 | Heilman et al. |
| 5,695,471 | A | 12/1997 | Wampler |
| 5,888,242 | A | 3/1999 | Antaki et al. |
| 5,904,646 | A | 5/1999 | Jarvik |
| 6,071,093 | A | 6/2000 | Hart |
| 6,116,862 | A | 9/2000 | Rau et al. |

(Continued)

FOREIGN PATENT DOCUMENTS

| | | |
|---|---|---|
| CN | 1288757 A | 3/2001 |
| EP | 1812094 | 8/2007 |

*Primary Examiner* — Matthew W Schall
(74) *Attorney, Agent, or Firm* — Kilpatrick Townsend & Stockton LLP

(57) ABSTRACT

A mechanical circulatory support system includes an implantable blood pump, an implantable prosthetic rib assembly, and an implantable drive cable. The prosthetic rib assembly includes a prosthetic rib segment and a percutaneous electrical connector mounted to the prosthetic rib segment. The prosthetic rib segment is configured to be mounted to a patient's rib in place of a resected segment of the patient's rib. The electrical connector includes a skin interface portion configured to interface with an edge of a skin aperture through the patient's skin. The electrical connector is configured to expose a connection port of the electrical connector via the skin aperture. The implantable power cable is connected with or configured to be connected with each of the blood pump and the percutaneous electrical connector for transferring electric power received by the percutaneous electrical connector to the blood pump.

20 Claims, 5 Drawing Sheets

(56) References Cited

U.S. PATENT DOCUMENTS

| | | |
|---|---|---|
| 6,186,665 B1 | 2/2001 | Maher et al. |
| 6,234,772 B1 | 5/2001 | Wampler et al. |
| 6,264,635 B1 | 7/2001 | Wampler et al. |
| 6,688,861 B2 | 2/2004 | Wampler |
| 6,991,595 B2 | 1/2006 | Burke et al. |
| 7,699,586 B2 | 4/2010 | LaRose et al. |
| 7,976,271 B2 | 7/2011 | Larose et al. |
| 7,997,854 B2 | 8/2011 | LaRose et al. |
| 8,007,254 B2 | 8/2011 | Larose et al. |
| 8,152,493 B2 | 4/2012 | Larose et al. |
| 8,323,174 B2 | 12/2012 | Jeevanandam et al. |
| 8,449,444 B2 | 5/2013 | Poirier |
| 8,506,471 B2 | 8/2013 | Bourque |
| 8,562,508 B2 | 10/2013 | Dague et al. |
| 8,597,350 B2 | 12/2013 | Rudser et al. |
| 8,652,024 B1 | 2/2014 | Yanai et al. |
| 8,657,733 B2 | 2/2014 | Ayre et al. |
| 8,668,473 B2 | 3/2014 | Larose et al. |
| 9,005,105 B2 | 4/2015 | Yomtov et al. |
| 2005/0071001 A1 | 3/2005 | Jarvik |
| 2007/0078293 A1 | 4/2007 | Shambaugh et al. |
| 2008/0021394 A1 | 1/2008 | Larose et al. |
| 2009/0203957 A1 | 8/2009 | Larose et al. |
| 2012/0045918 A1 | 2/2012 | Litzler et al. |
| 2012/0046514 A1 | 2/2012 | Bourque |
| 2012/0095281 A1 | 4/2012 | Reichenbach et al. |
| 2013/0096364 A1 | 4/2013 | Reichenbach et al. |
| 2013/0121821 A1 | 5/2013 | Ozaki et al. |
| 2013/0170970 A1 | 7/2013 | Ozaki et al. |
| 2013/0225909 A1 | 8/2013 | Dormanen et al. |
| 2013/0314047 A1 | 11/2013 | Eagle et al. |
| 2016/0129169 A1 | 5/2016 | Forsell | supporting a prosthetic rib segment via a patient's rib, the prosthetic rib segment being mounted to the patient's rib and occupying a volume that was occupied by a resected segment of the patient's rib - 102 supporting a percutaneous electrical connector via the prosthetic rib segment so as to expose a connection port of the electrical connector via an aperture through a skin portion of the patient, the percutaneous electrical connector being mounted to the prosthetic rib segment - 104 interfacing a skin interface portion of the percutaneous electrical connector and an edge of the aperture - 106 transferring electrical power from the external power source to the medical device via an external power cable connected to the connection port and an implanted power cable connected with the percutaneous electrical connector - 108

FIG. 6

PROSTHETIC RIB WITH INTEGRATED PERCUTANEOUS CONNECTOR FOR VENTRICULAR ASSIST DEVICES

CROSS-REFERENCES TO RELATED APPLICATIONS

This application claims the benefit of U.S. Provisional Application No. 62/380,081, filed Aug. 26, 2016, the entire contents of which are hereby incorporated by reference in its entirety for all purposes.

BACKGROUND

Ventricular assist devices, known as VADs, often include an implantable blood pump and are used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries and/or high blood pressure can leave a heart too weak to pump enough blood to the body. As symptoms worsen, advanced heart failure develops.

A patient suffering from heart failure may use a VAD while awaiting a heart transplant or as a long term destination therapy. A patient may also use a VAD while recovering from heart surgery. Thus, a VAD can supplement a weak heart (i.e., partial support) or can effectively replace the natural heart's function.

Long term use of a VAD, however, may result in undesirable complications. One of the most prevalent adverse events for patients under chronic mechanical circulatory support is infection. In existing VAD systems, a percutaneous power cable, which is often used to supply electrical power to the implanted blood pump, is the predominant source of such infections. While the use of a transcutaneous energy transfer system can be used to eliminate the need to use a percutaneous power cable, transcutaneous energy transfer systems are complicated and have the potential for associated adverse events.

In view of the benefits that the long-term use of a VAD can provide, improved VAD systems that have reduced occurrences of adverse advents relative to existing VAD systems are desired. In particular, improved VAD systems that include a percutaneous power cable with reduced potential for associated infection are desired.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Improved medical systems and related methods are described in which a bone-anchored connector assembly provides an externally accessible power connection port for supplying power to an implanted device (e.g., an implanted blood pump, for example, a VAD). The bone-anchored connector assembly extends through an aperture in the skin and interfaces with the skin around the aperture in stabilized manner in which relative movement between the bone-anchored connector assembly and the skin is inhibited, thereby reducing the potential for associated infection. In many embodiments, a bone structure of a patient (e.g., rib) is prepared so that the bone-anchored connector assembly replaces a portion of the bone structure. For example, in many embodiments, a short section of rib is resected and replaced by a rib-anchored connector assembly. The resection of the rib and the installation of the rib-anchored connector assembly to replace the resected portion of rib can be accomplished by a cardiovascular surgeon using relatively simple, established surgical procedures. The rib-anchored connector assembly provides the following advantages: (a) the rib-anchored connector can be configured to attach to the rib at opposing ends of the rib-anchored connector thereby enabling non-complicated replacement of the resected segment of the rib with the rib-anchored connector assembly; (b) the power line between the rib-anchored connector and the implanted device can be connected to the back of the rib-anchored connector, (c) the implantation of the rib-anchored connector assembly can be accomplished through a small thoracotomy in the upper quadrant that generally coincides with the incision made to expose the ascending aorta for attachment of the outflow cannula of a VAD to the ascending aorta, thereby obviating need for an additional incision; (d) implantation of the rib-anchored connector assembly in the upper quadrant is suitable for many common implanted devices (VAD, automatic implantable cardioverter-defibrillator (AICD), pacemaker); and (e) a rib-anchored connector assembly implanted in the upper quadrant can be easily seen and reached by the patient to make secure connections/disconnections and, importantly, to properly place a waterproof cap for periods of untethered operation.

Thus, in one aspect, a mechanical circulatory support system is described. The mechanical circulatory support system includes an implantable blood pump, an implantable prosthetic rib assembly, and an implantable power cable. The implantable blood pump is for generating a blood flow in a patient in which the blood pump is implanted. The implantable prosthetic rib assembly includes a prosthetic rib segment and a percutaneous electrical connector mounted to the prosthetic rib segment. The prosthetic rib segment is configured to be mounted to a rib of the patient in place of a resected segment of the rib. The percutaneous electrical connector includes a skin interface portion configured to interface with an edge of an aperture through a skin portion of the patient. The electrical connector is configured to expose a connection port of the electrical connector via the aperture. The implantable power cable is connected with or configured to be connected with each of the blood pump and the percutaneous electrical connector for transferring electric power received by the percutaneous electrical connector to the blood pump. In many embodiments, the skin interface portion of the electrical connector includes a circumferential recess for enhanced constraint of the interfacing skin.

In many embodiments, the percutaneous electrical connector is replaceable. For example, the percutaneous electrical connector can be configured to be demountable from the prosthetic rib segment to enable mounting of a replacement percutaneous electrical connector to the prosthetic rib segment.

In many embodiments, the distance from the prosthetic rib segment to the skin interface portion is adjustable to accommodate patient to patient variation. For example, the implantable prosthetic rib assembly can be reconfigurable to adjust a distance from the prosthetic rib segment to the skin interface portion to enable placement of the skin interface portion based on a location of the edge of the skin aperture. Any suitable approach can be used to adjust the distance from the prosthetic rib segment to the skin interface portion. For example, the implantable prosthetic rib assembly can include a replaceable fixed length portion that can be replaced with a replacement fixed length portion having a different length than the replaceable fixed length portion to adjust the distance from the prosthetic rib segment to the skin interface portion. As another example, the implantable prosthetic rib assembly can be configured to accommodate installation and/or removal of one or more spacers to adjust the distance from the prosthetic rib segment to the skin interface portion.

The connection port can have any suitable position and/or orientation relative to the patient. For example, the connection port can be substantially flush with an exterior surface of the skin portion of the patient when the skin interface portion is interfaced with the edge of the skin aperture. As another example, the connection port can be disposed proud of an exterior surface of the skin portion of the patient when the skin interface portion is interfaced with the edge of the skin aperture. As yet another example, the connection port can be oriented substantially parallel to the skin portion of the patient when the skin interface portion is interfaced with the edge of the skin aperture.

In another aspect, a method of transferring electrical power from an external power source to a medical device implanted in a patient is provided. The method includes supporting a prosthetic rib segment via a rib of the patient. The prosthetic rib segment is mounted to the rib and occupies a volume that was occupied by a resected segment of the rib. A percutaneous electrical connector is supported via the prosthetic rib segment so as to expose a connection port of the electrical connector via an aperture through a skin portion of the patient. The percutaneous electrical connector is mounted to the prosthetic rib segment. A skin interface portion of the percutaneous electrical connector is interfaced with an edge of the skin aperture. Electrical power is transferred from the external power source to the medical device via an external power cable connected to the connection port and an implanted power cable connected with the percutaneous electrical connector. In many embodiments of the method, the skin interface portion of the electrical connector includes a circumferential recess.

In many embodiments of the method, the percutaneous electrical connector is replaceable. For example, the percutaneous electrical connector can be demountable from the prosthetic rib segment to enable mounting of a replacement percutaneous electrical connector to the prosthetic rib segment.

In many embodiments of the method, the distance from the prosthetic rib segment to the skin interface portion is adjustable to accommodate patient to patient variation. For example, the implantable prosthetic rib assembly can be reconfigurable to adjust a distance from the prosthetic rib segment to the skin interface portion to enable placement of the skin interface portion based on a location of the edge of the skin aperture. Any suitable approach can be used to adjust the distance from the prosthetic rib segment to the skin interface portion. For example, in many embodiments of the method, the implantable prosthetic rib assembly includes a replaceable fixed length portion that can be replaced with a replacement fixed length portion having a different length than the replaceable fixed length portion to adjust the distance from the prosthetic rib segment to the skin interface portion. As another example, in many embodiments of the method, the implantable prosthetic rib assembly is configured to accommodate installation and/or removal of one or more spacers to adjust the distance from the prosthetic rib segment to the skin interface portion.

The method can be practiced with any connection port that has a suitable position and/or orientation relative to the patient. For example, the connection port can be substantially flush with an exterior surface of the skin portion of the patient when the skin interface portion is interfaced with the edge of the skin aperture. As another example, the connection port can be disposed proud of an exterior surface of the skin portion of the patient when the skin interface portion is interfaced with the edge of the skin aperture. As yet another example, the connection port can be oriented substantially parallel to the skin portion of the patient when the skin interface portion is interfaced with the edge of the skin aperture.

In another aspect, an implantable medical system includes an implantable medical device, an implantable prosthetic rib assembly, and an implantable power cable. The implantable prosthetic rib assembly includes a prosthetic rib segment and a percutaneous electrical connector mounted to the prosthetic rib segment. The prosthetic rib segment is configured to be mounted to a rib of the patient in place of a resected segment of the rib. The percutaneous electrical connector includes a skin interface portion configured to interface with an edge of a skin aperture through a skin portion of the patient. The electrical connector is configured to expose a connection port of the electrical connector via the skin aperture. The implantable power cable is connected with or configured to be connected with each of the medical device and the percutaneous electrical connector for transferring electric power received by the percutaneous electrical connector to the medical device. In many embodiments of the implantable medical system, the skin interface portion of the electrical connector includes a circumferential recess.

The implantable medical device can have suitable combination of additional features and/or attributes. For example, the percutaneous electrical connector can be demountable from the prosthetic rib segment to enable mounting of a replacement percutaneous electrical connector to the prosthetic rib segment. The implantable prosthetic rib assembly can be reconfigurable to adjust a distance from the prosthetic rib segment to the skin interface portion to enable placement of the skin interface portion based on a location of the edge of the skin aperture. For example, the implantable prosthetic rib assembly can include a replaceable fixed length portion that can be replaced with a replacement fixed length portion having a different length than the replaceable fixed length portion to adjust the distance from the prosthetic rib segment to the skin interface portion. As another example, the implantable prosthetic rib assembly can be configured to accommodate installation and/or removal of one or more spacers to adjust the distance from the prosthetic rib segment to the skin interface portion. The connection port can have any suitable position and/or orientation. For example, the connection port can be substantially flush with an exterior surface of the skin portion of the patient when the skin interface portion is interfaced with the edge of the skin aperture. As another example, the connection port can be disposed proud of an exterior surface of the skin portion of the patient when the skin interface portion is interfaced with the edge of the skin aperture. As yet another example, the connection port can be oriented substantially parallel to the skin portion of the patient when the skin interface portion is interfaced with the edge of the skin aperture.

For a fuller understanding of the nature and advantages of the present invention, reference should be made to the ensuing detailed description and accompanying drawings.

BRIEF DESCRIPTION OF THE DRAWINGS

FIG. 6 is a simplified block diagram of acts of a method for transferring power from an external power source to an implanted medical device via a rib-mounted prosthetic rib assembly that includes a percutaneous electrical connector, in accordance with many embodiments.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
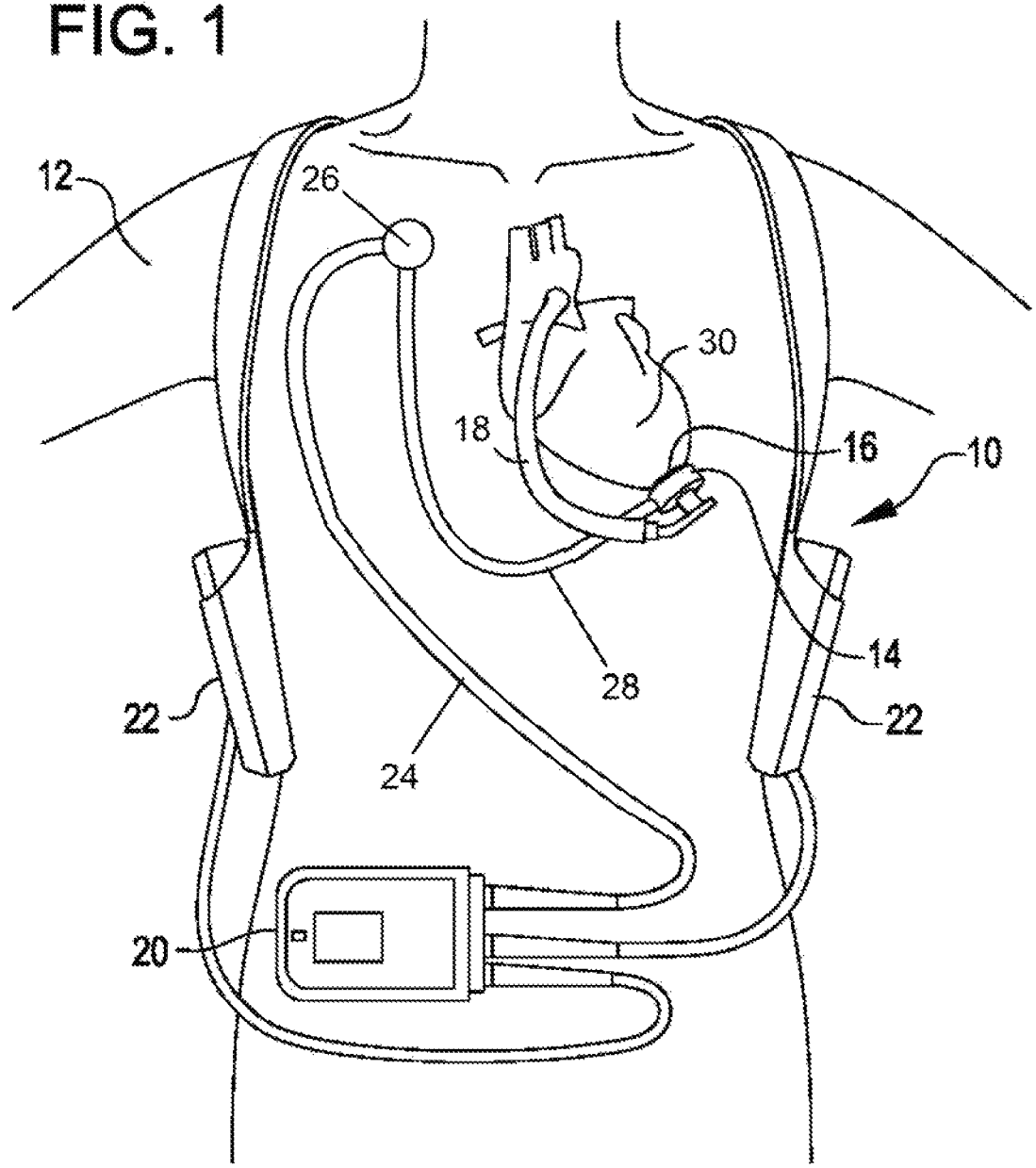
FIG. 1 is an illustration of a mechanical circulatory support system, which includes a prosthetic rib assembly, implanted in a patient's body, in accordance with many embodiments.

Referring now to the drawings, in which like reference numerals represent like parts throughout the several views, FIG. 1 is an illustration of a mechanical circulatory support system 10 implanted in a patient 12. The mechanical circulatory support system 10 includes an implantable blood pump assembly 14, a ventricular cuff 16, an outflow cannula 18, an external system controller 20, power sources 22, an external drive line 24, a prosthetic rib assembly 26, and an implanted drive line 28. The implantable blood pump assembly 14 can include a VAD that is attached to an apex of the left ventricle, as illustrated, or the right ventricle, or both ventricles of the heart 30. The VAD can include a centrifugal pump (as shown) that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668.473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety.

The blood pump assembly 14 can be attached to the heart 30 via the ventricular cuff 16, which can be sewn to the heart 30 and coupled to the blood pump 14. The other end of the blood pump 14 connects to the ascending aorta via the outflow cannula 18 so that the VAD effectively diverts blood from the weakened ventricle and propels it to the aorta for circulation through the rest of the patient's vascular system.

FIG. 1 illustrates the mechanical circulatory support system 10 during battery 22 powered operation. The blood pump 14 is operatively connected with the external controller 20 and the batteries 22 via the external drive line 24, the prosthetic rib assembly 26, and the implanted drive line 28. As described in more detail herein, the prosthetic rib assembly 26 is attached to a rib of the patient 12 in place of a resected segment of the rib. The prosthetic rib assembly 26 includes a percutaneous electrical connector that is connected with the implanted drive line 28 and connectable with the external drive line 24 for the transfer of electrical power and/or one or more control signals from any suitable external source (e.g., the battery 22, the external system controller 20) to the blood pump 14. The percutaneous electrical connector of the prosthetic rib assembly 26 extends through an aperture in the patient's skin. The external system controller 20 monitors operation of the mechanical circulatory support system 10. Related controller systems applicable to the present invention are described in greater detail below and in U.S. Pat. Nos. 5,888,242, 6,991,595, 8,323,174, 8,449,444, 8,506,471, 8,597,350, and 8,657,733, EP 1812094, and U.S. Patent Publication Nos. 2005/0071001 and 2013/0314047, all of which are incorporated herein by reference for all purposes in their entirety. The system 10 can be powered by either one, two, or more batteries 22.

The mechanical circulatory support system 10 can also include an internal controller assembly and one or more internal rechargeable power storage devices that are configured and operatively coupled between the prosthetic rib assembly 26 and the blood pump 14 via the implanted drive line 28 to enable untethered operation of the system 10. For example, the mechanical circulatory support system 10 can include an internal controller as assembly described in U.S. Pat. No. 8,562,508, all of which is incorporated herein by reference for all purposes in their entirety.

Figure 2:
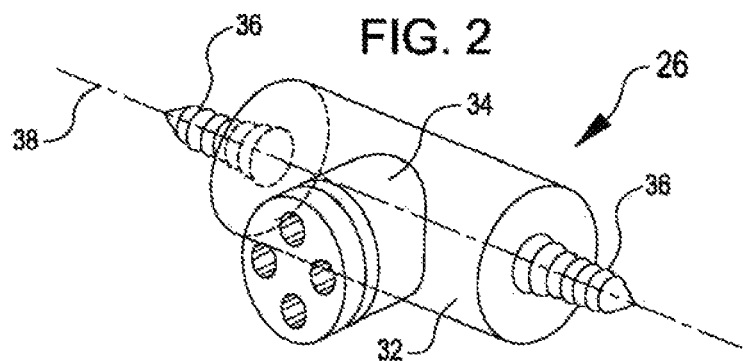
FIG. 2 is an illustration of the prosthetic rib assembly that includes a percutaneous electrical connector, in accordance with many embodiments.

FIG. 2 illustrate an embodiment of the prosthetic rib assembly 26. In the illustrated embodiment, the prosthetic rib assembly 26 includes a prosthetic rib segment 32 and a percutaneous electrical connector 34 attached or mounted to the prosthetic rib segment 32. In many embodiments, the prosthetic rib segment 32 is configured to be mounted in place of a resected section of the patient's rib. In the illustrated embodiment, the prosthetic rib segment 32 includes mounting studs 36 extending from opposite ends of the prosthetic rib segment 32. The mounting studs 36 are coaxial with a mounting stud axis 38 and extend in opposite directions. The mounting studs 36 include self-tapping threads with one reverse-direction thread so that the prosthetic rib assembly 26 can be mounted in place of a resected rib segment via rotation of the prosthetic rib assembly 26 around the mounting stud axis 38 to screw the mounting studs 36 into the exposed rib ends resulting from the resection of the rib segment.

Figure 3:
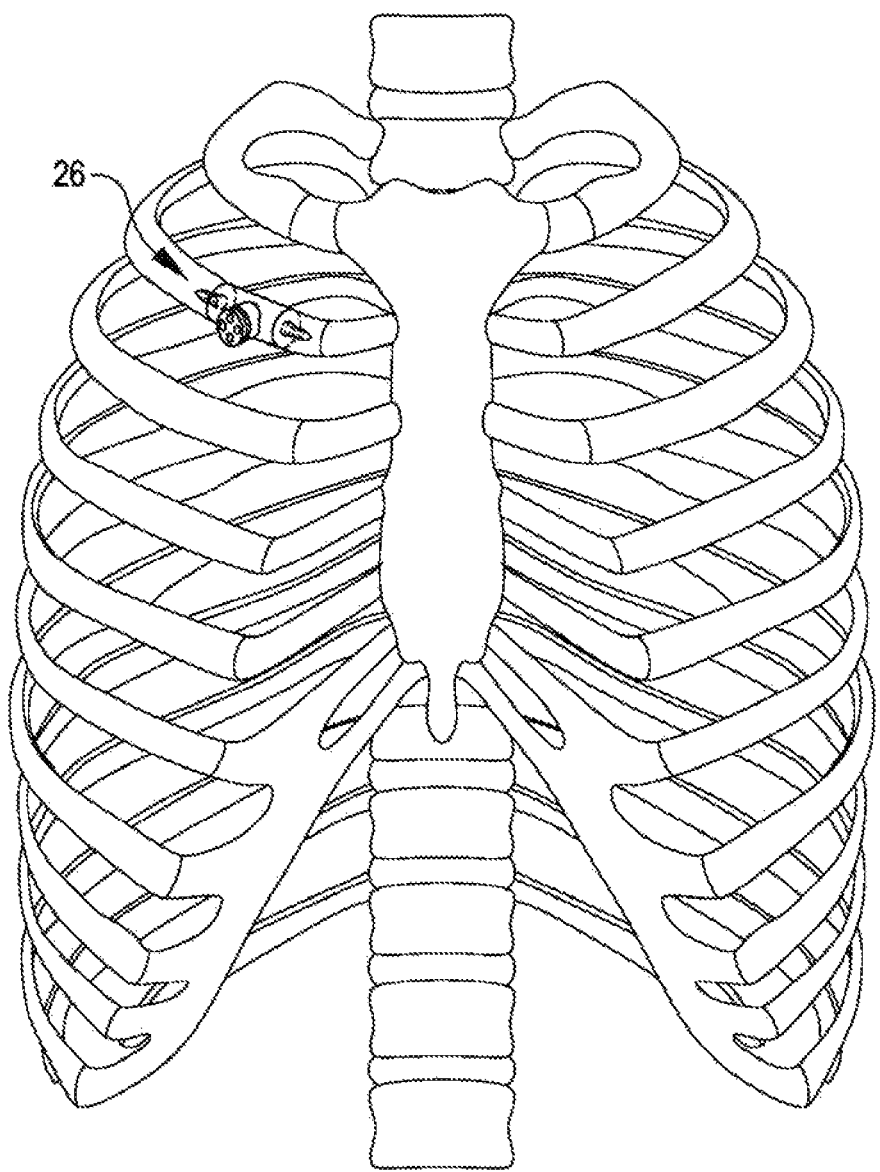
FIG. 3 illustrates the prosthetic rib assembly of FIG. 2 implanted in a patient's body.

In many embodiments, the percutaneous electrical connector 34 is connectable with each of the external drive line 24 and the implanted drive line 28 to operatively couple conductors of the external drive line 24 with respective conductors of the implanted drive line 28. Accordingly, the prosthetic rib assembly 26 can be separately rotated around the mounting stud axis 28 to screw the mounting studs into the exposed rib ends with the implanted drive line 28 disconnected and the implanted drive line 28 connected to the percutaneous electrical connector 34 after the prosthetic rib assembly 26 is mounted to the exposed rib ends. FIG. 3 illustrates the prosthetic rib assembly of FIG. 2 implanted in a patient's body. The external drive line 24 can then be selectively coupled with the electrical connector 34 and selectively decoupled from the electrical connector 34.

Figure 4:
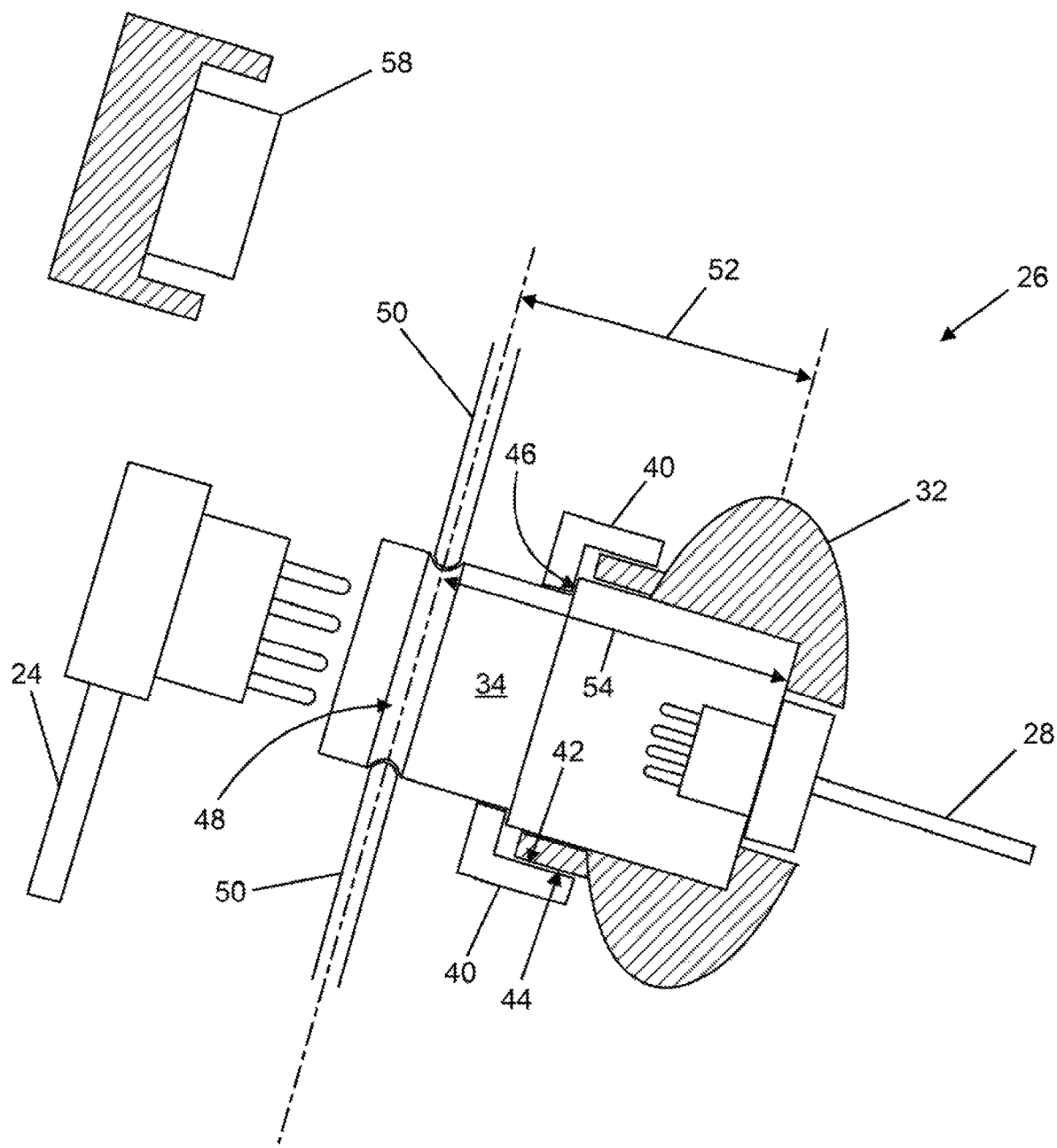
FIG. 4 is an illustration of a prosthetic rib assembly, which includes a percutaneous electrical connector and can be configured to account for patient to patient variation in rib to skin distance, in accordance with many embodiments.

FIG. 4 shows a cross-sectional view of an embodiment of the prosthetic rib assembly 26 in an implanted state and connected with the implanted drive line 28. In the illustrated embodiment, the prosthetic rib assembly 26 includes the prosthetic rib segment 32, the transcutaneous electrical connector 34, and a coupling element 40. The electrical connector 34 is accommodated within a recess in the prosthetic rib segment 32. The coupling element 40 is configured for use in securing the electrical connector 34 to the prosthetic rib segment 32. In the illustrated embodiment, the coupling element 40 includes female threads 42 that engage male threads 44 included the prosthetic rib segment 32. The coupling element 40 engages a shoulder 46 of the electrical connector 34 thereby securing the electrical connector 34 to the prosthetic rib segment 32. Any suitable approach can be used to mount the electrical connector 34 to the prosthetic rib segment 32.

In the illustrated embodiment, the electrical connector 34 includes a circumferential recessed skin interface portion 48 that is configured to interface with the edge of an aperture through the skin 50 of the patient 12. The edge of the aperture through the skin 50 extends into the recessed skin interface portion 48 thereby helping to inhibit relative movement between the interfacing aperture of the skin 50 and the recessed skin interface portion 48.

Figure 5:
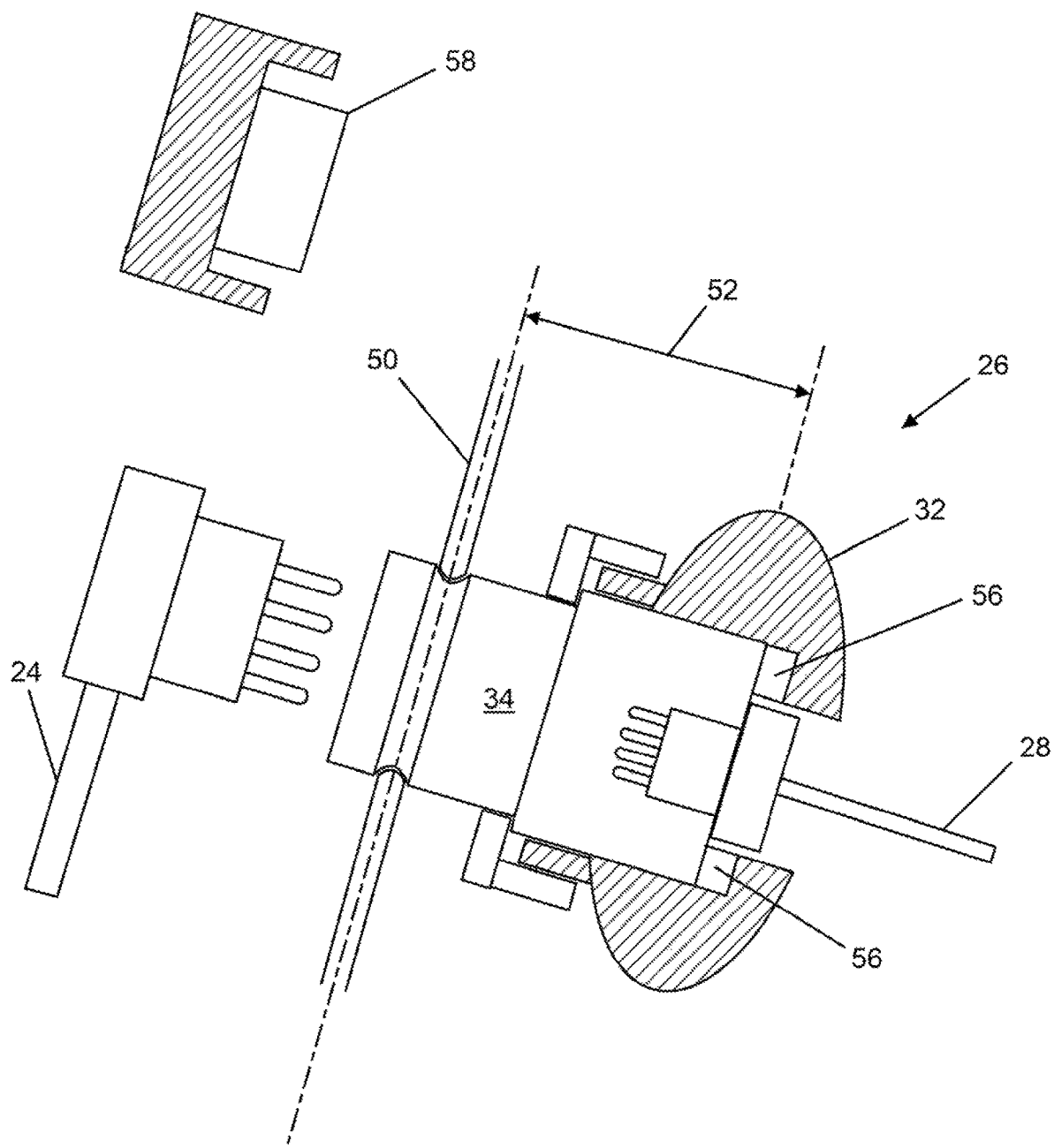
FIG. 5 is an illustration of another prosthetic rib assembly, which includes a percutaneous electrical connector and can be adjusted to account for patient to patient variation in rib to skin distance, in accordance with many embodiments.

In many embodiments, the prosthetic rib assembly 26 is configurable to have a rib to skin offset distance 52 suitable for a particular patient 12. For example, in the embodiment illustrated in FIG. 4, the electrical connector 34 can be selected from a series of electrical connectors 34, each having a different length 54, to produce a desired rib to skin offset distance 52. The ability to vary the rib to skin offset distance 52 provides the ability to accommodate patient to patient variability with respect to distance between the rib of the patient 12 and the skin 50 as well as variability in the implanted location of the prosthetic rib segment 32 relative to the rib of the patient 12. As another example, in the embodiment illustrated in FIG. 5, the thickness of a shim(s) 56 can be adjusted to produce a desired rib to skin offset distance 52.

In many embodiments, the prosthetic rib assembly 26 includes a water-proof cap 58 for inhibiting and ideally preventing ingress of water into the electrical connector 34 when coupled with the electrical connector 34. For example, the water-proof cap 58 can be coupled with the electrical connector 34 during a period of untethered operation. For example, the external drive line 24 can be decoupled from the electrical connector 34 and the water-proof cap 58 configured to be mounted to the electrical connector 34 and shield a connection port of the electrical connector 34 from moisture ingression during showing or bathing by the patient.

FIG. 6 is a simplified block diagram of acts of a method 100 for transferring power from an external power source to an implanted medical device via a rib-mounted prosthetic rib assembly that includes a percutaneous electrical connector, in accordance with many embodiments. Any suitable rib-mounted prosthetic rib assembly, such as the prosthetic rib assembly 26 embodiments described herein, can be used to practice the method 100.

The method 100 includes supporting a prosthetic rib segment via a rib of a patient (act 102). In many embodiments of the method 100, the prosthetic rib segment is mounted to the patient's rib and occupies a volume that was occupied by a resected segment of the patient's rib.

The method 100 includes supporting a percutaneous electrical connector via the prosthetic rib segment so as to expose a connection port of the electrical connector via an aperture through a skin portion of the patient (act 104). In many embodiments of the method 100, the percutaneous electrical connector is mounted to the prosthetic rib segment.

The method 100 includes interfacing a skin interface portion of the percutaneous electrical connector and an edge of the aperture (act 106). In many embodiments of the method 100, interfacing the skin interface portion of the electrical connector and the edge of the aperture in the skin inhibits relative movement between the patient's skin and the electrical connector, thereby helping to inhibit the development of infection induced via relative movement between the skin and the electrical connector.

The method 100 includes transferring electrical power from the external power source to the medical device via an external power cable connected to the connection port and an implanted power cable connected with the percutaneous electrical connector (act 108). In many embodiments of the method 100, the external power cable can be selectively coupled to and decoupled from the percutaneous electrical connector.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A mechanical circulatory support system, comprising:
   an implantable blood pump for generating a blood flow in a patient in which the blood pump is implanted;
   an implantable prosthetic rib assembly including a prosthetic rib segment and a percutaneous electrical connector mounted to the prosthetic rib segment, the prosthetic rib segment being shaped to simulate and replace a length of a rib of the patient, the prosthetic rib segment having a first end and a second end opposite to the first end, each of the first end and the second end being configured for attachment to a respective exposed end of the rib resulting from resection of the length of the rib, the percutaneous electrical connector including a skin interface portion configured to interface with an edge of a skin aperture through a skin portion of the patient, the electrical connector being configured to expose a connection port of the electrical connector via the skin aperture; and
   an implantable power cable connected with or configured to be connected with each of the blood pump and the percutaneous electrical connector for transferring electric power received by the percutaneous electrical connector to the blood pump.

2. The mechanical circulatory support system of claim 1, wherein the percutaneous electrical connector is demountable from the prosthetic rib segment to enable mounting of a replacement percutaneous electrical connector to the prosthetic rib segment.

3. The mechanical circulatory support system of claim 1, wherein the implantable prosthetic rib assembly is reconfigurable to adjust a distance from the prosthetic rib segment to the skin interface portion to enable placement of the skin interface portion based on a location of the edge of the skin aperture.

4. The mechanical circulatory support system of claim 3, wherein the implantable prosthetic rib assembly comprises a replaceable fixed length portion that can be replaced with a replacement fixed length portion having a different length than the replaceable fixed length portion to adjust the distance from the prosthetic rib segment to the skin interface portion.

5. The mechanical circulatory support system of claim 3, wherein the implantable prosthetic rib assembly is configured to accommodate installation and/or removal of one or more spacers to adjust the distance from the prosthetic rib segment to the skin interface portion.

6. The mechanical circulatory support system of claim 1, wherein the connection port is substantially flush with an exterior surface of the skin portion of the patient when the skin interface portion is interfaced with the edge of the skin aperture.

7. The mechanical circulatory support system of claim 1, wherein the connection port is disposed proud of an exterior surface of the skin portion of the patient when the skin interface portion is interfaced with the edge of the skin aperture.

8. The mechanical circulatory support system of claim 1, wherein the connection port is oriented substantially parallel to the skin portion of the patient when the skin interface portion is interfaced with the edge of the skin aperture.

9. The mechanical circulatory support system of claim 1, wherein the skin interface portion of the electrical connector includes a circumferential recess.

10. The mechanical circulatory support system of claim 1, further comprising a water proof cap configured to be mounted to the percutaneous electrical connector and shield the connection port from moisture ingression during showering or bathing by the patient.

11. An implantable medical system, comprising:
    an implantable medical device;
    an implantable prosthetic rib assembly including a prosthetic rib segment and a percutaneous electrical connector mounted to the prosthetic rib segment, the prosthetic rib segment being shaped to simulate and replace a length of a rib of the patient, the prosthetic rib segment having a first end and a second end opposite to the first end, each of the first end and the second end being configured for attachment to a respective exposed end of the rib resulting from resection of the length of the rib, the percutaneous electrical connector including a skin interface portion configured to interface with an edge of a skin aperture through a skin portion of the patient, the electrical connector being configured to expose a connection port of the electrical connector via the skin aperture; and
    an implantable power cable connected with or configured to be connected with each of the medical device and the percutaneous electrical connector for transferring electric power received by the percutaneous electrical connector to the medical device.

12. The implantable medical system of claim 11, wherein at least one of:
    the percutaneous electrical connector is demountable from the prosthetic rib segment to enable mounting of a replacement percutaneous electrical connector to the prosthetic rib segment;
    the implantable prosthetic rib assembly is reconfigurable to adjust a distance from the prosthetic rib segment to the skin interface portion to enable placement of the skin interface portion based on a location of the edge of the skin aperture;
    the implantable prosthetic rib assembly comprises a replaceable fixed length portion that can be replaced with a replacement fixed length portion having a different length than the replaceable fixed length portion to adjust the distance from the prosthetic rib segment to the skin interface portion;
    the implantable prosthetic rib assembly is configured to accommodate installation and/or removal of one or more spacers to adjust the distance from the prosthetic rib segment to the skin interface portion;

the connection port is substantially flush with an exterior surface of the skin portion of the patient when the skin interface portion is interfaced with the edge of the skin aperture;

the connection port is disposed proud of an exterior surface of the skin portion of the patient when the skin interface portion is interfaced with the edge of the skin aperture;

the connection port is oriented substantially parallel to the skin portion of the patient when the skin interface portion is interfaced with the edge of the skin aperture;

the skin interface portion of the electrical connector includes a circumferential recess; and the percutaneous electrical connector comprises a water proof cap configured to be mounted to the percutaneous electrical connector and shield the connection port from moisture ingression during showering or bathing by the patient.

13. An implantable prosthetic rib assembly comprising:

a prosthetic rib segment shaped to simulate and replace a length of a rib of the patient, the prosthetic rib segment having a first end and a second end opposite to the first end, each of the first end and the second end being configured for attachment to a respective exposed end of the rib resulting from resection of the length of the rib; and an electrical connector mounted to the prosthetic rib segment and including a skin interface portion configured to interface with an edge of a skin aperture through a skin portion of the patient, the electrical connector being configured to expose a connection port of the electrical connector via the skin aperture.

14. The implantable prosthetic rib assembly of claim 13, wherein the electrical connector includes a second connection port configured to be connected with an implantable electrical cable.

15. The mechanical circulatory support system of claim 1, wherein the prosthetic rib segment comprises:

a first mounting stud extending from the first end; and a second mounting stud extending from the second end, the second mounting stud being coaxial with the first mounting stud and a mounting stud axis.

16. The mechanical circulatory support system of claim 15, wherein:

the first mounting stud comprises a first self-tapping thread;

the second mounting stud comprises a second self-tapping thread; and the second self-tapping thread has a reversed direction relative to the first self-tapping thread so that the prosthetic rib segment can be mounted to the exposed ends of the rib via rotation of the prosthetic rib segment around the mounting stud axis.

17. The implantable medical system of claim 11, wherein the prosthetic rib segment comprises:

a first mounting stud extending from the first end; and a second mounting stud extending from the second end, the second mounting stud being coaxial with the first mounting stud and a mounting stud axis.

18. The implantable medical system of claim 17, wherein:

the first mounting stud comprises a first self-tapping thread;

the second mounting stud comprises a second self-tapping thread; and the second self-tapping thread has a reversed direction relative to the first self-tapping thread so that the prosthetic rib segment can be mounted to the exposed ends of the rib via rotation of the prosthetic rib segment around the mounting stud axis.

19. The implantable prosthetic rib assembly of claim 13, wherein the prosthetic rib segment comprises:

a first mounting stud extending from the first end; and a second mounting stud extending from the second end, the second mounting stud being coaxial with the first mounting stud and a mounting stud axis.

20. The implantable prosthetic rib assembly of claim 19, wherein:

the first mounting stud comprises a first self-tapping thread;

the second mounting stud comprises a second self-tapping thread; and the second self-tapping thread has a reversed direction relative to the first self-tapping thread so that the prosthetic rib segment can be mounted to the exposed ends of the rib via rotation of the prosthetic rib segment around the mounting stud axis.

* * * * *